United States Patent [19]
Robbins

[11] Patent Number: 4,823,799
[45] Date of Patent: Apr. 25, 1989

[54] BIOFEEDBACK INTERFACE FOR SENSORY ENHANCEMENT OF THE PLANTAR SURFACE OF THE FOOT

[76] Inventor: Stevens E. Robbins, 388 Olivier, Apt. 8, Westmount, Quebec, Canada, H3Z 2C9

[21] Appl. No.: 170,690

[22] Filed: Mar. 14, 1988

Related U.S. Application Data

[63] Continuation of Ser. No. 840,948, Jul. 31, 1986, abandoned.

[51] Int. Cl.⁴ ............................ A43B 5/06; A43B 7/00
[52] U.S. Cl. .................................. 128/581; 128/582; 36/44; 36/129
[58] Field of Search ................. 128/582, 581; 36/11.5, 36/83, 129, 114, 43, 44

[56] References Cited
U.S. PATENT DOCUMENTS

| | | |
|---|---|---|
| 171,987 | 1/1876 | Burke ........................................ 36/43 |
| 1,210,066 | 12/1916 | Hara ..................................... 36/43 X |
| 1,528,648 | 3/1925 | Armstrong ........................ 273/81 B |
| 2,356,490 | 8/1944 | Crotty ................................. 36/43 X |
| 2,378,039 | 6/1945 | Schenker . |
| 2,400,023 | 5/1946 | Potter . |
| 2,523,637 | 9/1950 | Stanfield et al. .................. 273/75 X |
| 2,734,286 | 2/1956 | Anson . |
| 2,758,382 | 8/1956 | Hurd . |
| 3,258,859 | 7/1966 | Lamont et al. ................. 128/582 X |
| 3,513,698 | 5/1970 | Ross . |
| 3,595,244 | 7/1971 | Kugler . |
| 3,757,774 | 9/1973 | Hatuno . |
| 3,992,788 | 11/1976 | Orien et al. . |
| 4,033,054 | 7/1977 | Fukuoka . |
| 4,047,310 | 9/1977 | Sunoo .................................... 36/11.5 |
| 4,095,353 | 6/1978 | Foldes .................................. 36/11.5 |
| 4,109,661 | 8/1978 | Fukuoka . |
| 4,321,752 | 3/1982 | Kaufman . |
| 4,345,387 | 8/1982 | Daswick ................................. 36/43 |
| 4,635,385 | 1/1987 | Ogden ............................... 36/3 B X |

FOREIGN PATENT DOCUMENTS

| | | |
|---|---|---|
| 193805 | 9/1986 | European Pat. Off. ............. 36/11.5 |
| 1485683 | 4/1970 | Fed. Rep. of Germany ...... 128/582 |
| 2024534 | 12/1971 | Fed. Rep. of Germany ....... 36/11.5 |
| 2619410 | 11/1976 | Fed. Rep. of Germany . |
| 2046579 | 11/1980 | United Kingdom ................. 36/11.5 |
| 2124473 | 2/1984 | United Kingdom ..................... 36/43 |

*Primary Examiner*—Clifford D. Crowder
*Attorney, Agent, or Firm*—Larson and Taylor

[57] ABSTRACT

The present invention relates to a method and a device for preventing injuries resulting from overloading the plantar surface of an individual during an intense physical activity such as locomotion, jumping or the like. More specifically, the invention relates to a biofeedback interface to be interposed between the plantar surface and the ground surface. The biofeedback interface functions to substantially enhance the specific unpleasant sensations perceived by the individual during heavy plantar surface loading (locomotion and jumping) which are required to produce an enhanced protective behavioral response; the behavior avoids the unpleasant sensation, which in turn, decreases the loading with a reduction in the risk of physical injury.

8 Claims, 3 Drawing Sheets

BIOFEEDBACK INTERFACE FOR SENSORY ENHANCEMENT OF THE PLANTAR SURFACE OF THE FOOT

This application is a continuation, of application Ser. No. 890,948 filed July 31, 1986, now abandoned.

FIELD OF THE INVENTION

The present invention relates generally to the field of injury prevention and, more particularly, to a biofeedback interface adapted to be interposed between the plantar surface and the ground to enhance the sensation perceived by the individual during heavy plantar surface loading to produce enhanced protective behavioral response.

The invention also relates to a method for preventing injury resulting from intense physical activity such as locomotion, jumping or the like.

BACKGROUND OF THE INVENTION

The plantar surface of the human body possesses a dense concentration of mechanoreceptors and nociceptors which respond to certain types of mechanical forces. These receptors input information to the nervous system which often results in a behavioral response. This is a form of sensory feedback control, which in the case of the plantar surface, certainly protects against injury to the lower extremity and probably to the body as a whole.

The examination of protective behavior related to heavy loading of the plantar surface has been the subject of research performed by the inventor. In performing this research, the inventor discovered feedback control mechanisms which are, in essence, protective behavior in the form of avoidance behavior; i.e., a desire to minimize discomfort by moving away from what produces offensive sensation. The inventor has shown that while these mechanisms appear to play an important role in prevention of injuries during intense physical activity such as locomotion, jumping or the like in barefoot populations on natural surfaces, they are not used extensively in shod populations. The inventor has found that current footwear design is responsible for the reduced level of protective sensory feedback control and many injuries to shod populations that occur during locomotion or jumping. The inventor has found this to particularly be the case in individuals wearing athletic footwear of current design which incorporates a smooth, low friction layer in contact with the plantar surface, which remains regular even when loaded.

The inventor has discovered that the irregularities of natural surfaces produce localized skin deformations which are important in inducing the sensory feedback control mechanisms in barefoot populations, and the lack of surface irregularities, as well as diminished shear and movement of the plantar surface when in footwear, are responsible for reduced use sensory feedback control mechanisms in shod populations, and resulting overloading and injury that follow, by the same mechanisms as neuropathic injuries which are commonly seen in medicine.

OBJECTS AND STATEMENT OF THE INVENTION

An object of the invention is a device to be interposed between the plantar surface and the ground to interact with the human body for the prevention of injuries to the body resulting from intense physical activity such as locomotion, jumping or the like.

Another object of the invention is a method for the prevention of injuries resulting from intense physical activity such as locomotion, jumping or the like.

The objects of this invention are achieved by providing a biofeedback interface placed under the plantar surface while wearing footwear, as to effect a specific pattern of local plantar deformations, which produces sensation, in turn, objectively inducing avoidance behavior, the magnitude of which is directly related with the magnitude of load which the plantar surface experiences.

The biofeedback interface produces specific unpleasant sensation up to the level of pain (in high load ranges) which will induce the individual to avoid the biofeedback interface thus diminishing load during intense physical activity such as locomotion, jumping or the like.

In a preferred embodiment, the biofeedback interface is a layer with irregularities of particular design (height, spacing, rigidity, shape), as to produce the local plantar deformations to enhance perceived plantar surface load magnitude for, in turn, enhancing avoidance behavior. This is in contrast to existing devices and footwear that also utilize irregularities but are specifically designed to produce pleasurable sensation with their use, such as "massage", "relaxation" or the like.

In addition, the biofeedback interface may utilize low friction material which encourages movement across the irregularities, which constitutes an additional useful design characteristic.

The specific characteristics of the biofeedback interface are related greatly to the existence of, and physical properties of the additional layers (of footwear and socks) that separate the irregularities of the biofeedback interface from the plantar surface, the type of footwear in which it is installed and the magnitude of the force when it is used. With so many variables, the inventor has depended on experimental testing techniques to develop particular biofeedback interfaces; i.e., to see if they produce the desired protective behavior. Through the construction and testing of numerous designs, the inventor has found certain solutions incorporating a pattern of construction and design features which have been regularly successful in producing avoidance behavior, which will be discussed hereinafter.

In a broad sense, the present invention resides in the provision of a biofeedback interface for use with athletic footwear adapted to receive a foot of an individual and including a weightbearing surface on which the foot is supported, the athletic footwear being used for performing an intense physical activity such as locomotion, jumping or the like which produces high level of loading on the plantar surface of the foot producing a susceptibility to injury of the individual, the biofeedback interface being adapted to be mounted between the foot and the weightbearing surface and comprising means for producing a plurality of local plantar deformations for substantially enhancing the sensation perceived by the individual potentially up to pain level at the high level of loading for inducing a feedback reaction by the individual tending to adopt a posture for reducing the level of sensation perceived by the individual resulting in a moderation of the loading on the foot.

The invention also involves a method for reducing the risk of injury to an individual resulting from overloading the plantar surface of a foot of the individual during intense physical activity such as locomotion, jumping or the like performed with said foot received into an athletic footwear, the method comprising the step of creating a plurality of local plantar deformations on the plantar surface of the foot for substantially enhancing the sensation perceived by the individual potentially up to pain level during the intense physical activity such as locomotion, jumping or the like, the sensation enhancement inducing a feedback reaction by the individual tending to adopt a posture for reducing the level of sensation perceived by the individual resulting in a moderation of the loading on the foot.

DESCRIPTION OF PREFERRED EMBODIMENTS

Figure 1A:
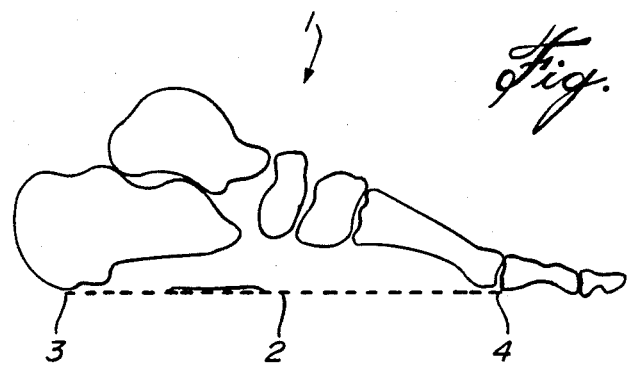
FIG. 1a is a schematic view illustrating the posture of a shod foot, the shoe being omitted.

The posture of a normally shod human foot 1 is shown in FIG. 1a. Foot 1 rests flat on the supporting surface 2 of a shoe (not shown), the load being distributed mainly on the heel portion 3 and the portion 4 of the foot under the metatarsal-phalangeal joints.

Figure 1B:
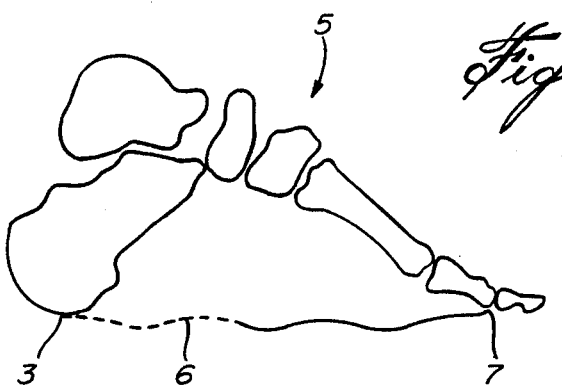
FIG. 1b is a schematical view of the posture of an unshod foot.

Referring to FIG. 1b, a normally unshod foot 5, resting on the ground 6 has an arched position, and contrary to shod foot 1, little or no load is exerted on the portion 4 of the foot under the metatarsal-phalangeal joints, the load being transferred on the digits 7. The shifting of the high loading zone from the portion 4 toward the digits 7 may be explained by the fact that the portion 4 under the metatarsal-phalangeal joints is more sensitive to mechanically induced sensation and the individual reacts, to the increased sensation when sensing the irregularities of the ground, by adopting an arched position to reduce the level of sensation perceived by the foot. This reaction is unlikely to occur in a normally shod foot since the numerous padding layers of the shoe and the contoured interior increase contact area, both of which reduce the sensation transmitted from the ground.

The posture of the foot shown in FIG. 1b provides a shock absorbing action limiting, to a certain extent, the stresses transmitted to the ligaments and the bones of the foot. On the contrary, a shod foot, resting flatly in the shoe, does not provide a shock absorbing action, transmitting directly all the stresses and increasing the risk of an injury.

When footwear incorporating the biofeedback interface, according to the invention, is used, sensory information is normally transmitted to the body, thus producing the avoidance behavioral response observed when performing the physical activity barefoot.

Embodiments of the present invention will now be described in detail.

Figure 2:
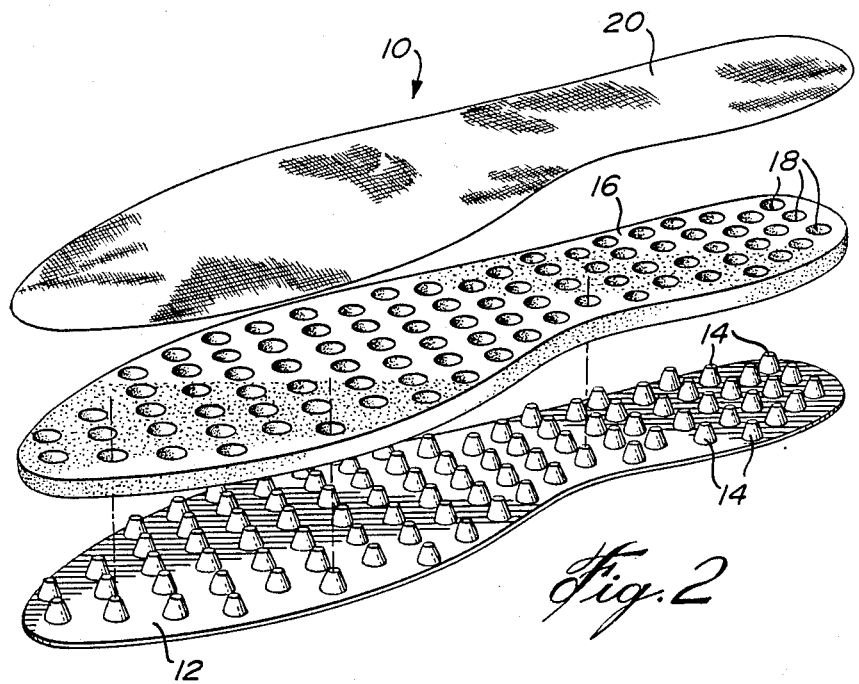
FIG. 2 is an exploded perspective view of a multi-layered biofeedback interface in the form of an insole for athletic footwear.

Referring to FIG. 2, the biofeedback interface designated generally by the reference numeral 10, is in the form of an insole to be interposed between the foot and the weightbearing surface of a shoe. The insole is in general cut to the outline of the perimeter of the plantar surface of the foot and comprises a base member 12 of a relatively rigid plastic material including a plurality of upwardly extending projections 14 defining a highly irregular surface. The size and the spacing of projections 14 are not critical to the invention as long as they provide the desired level of sensory enhancement. Also there may be projections of single or multiple shape. Projections having a height of 5 mm and an interspacing of 15 mm have been found satisfactory. However, these values will vary from one application to another as well as from one individual to another, to achieve optimum results.

A layer of foamed plastic material 16, is fixed on the base member 12, the top of projections 14 being substantially flush with the top surface of foam-like layer 16 which is provided with a series of openings 18 to receive the projection 14.

A top layer 20 made of low friction fabric is mounted on foam layer 16 and covers the top of projections 14. Layers 16, 20 and base member 12 form an unitary structure.

Foam-like layer 16 and top fabric layer 10 are not essential to the invention and are used mainly to prevent the foot from making direct contact with the projections 14 and avoid blistering of the skin. It may very well be envisaged to form the projections 14 smaller to avoid using the foam layer 16 and the fabric layer 20.

The biofeedback interface 10 will substantially augment the sensation perceived by the foot and will be appreciated by the wearer of the shoe as increased discomfort especially when the load of the foot is very high. With this information, a variety of responses can occur including the adoption of a more arched position in the shoe, providing a shock absorbing action, or the individual will avoid the discomfort by running with less vertical force, both of which moderate the impact on the foot for reducing the risk of injuries.

Figure 3:
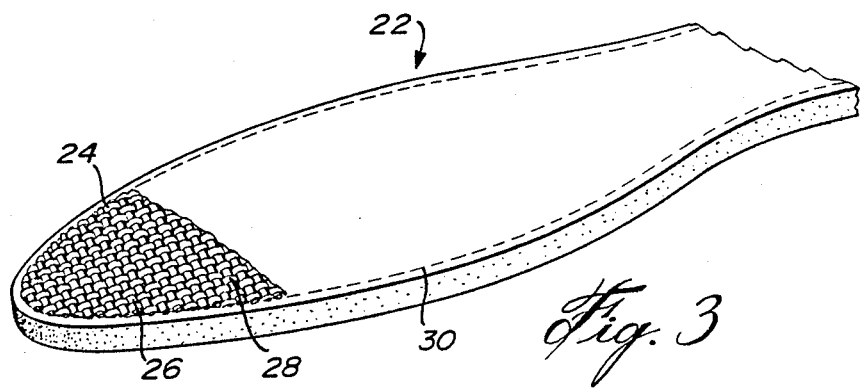
FIG. 3 is a perspective view of a single layer biofeedback interface having a woven structure, still for footwear application.

FIG. 3 illustrates another embodiment of a biofeedback interface 22 for footwear which is an alternative to the biofeedback interface 10. Biofeedback interface 22 defines an insole constituted by a woven structure 24 which includes a plurality of threads defining at their intersections alternating depressions 26 and projections 28 which form a highly irregular surface for substantially enhancing the sensation perceived by the individual. Woven structure 24 has a shape corresponding to the sole of a foot and on the periphery is sewn a strip 30 of fabric for holding the threads together and preventing them from breaking loose.

In FIG. 3, the woven structure has been shown to cover only a portion of the insole, for simplicity. However, it should be clearly understood that the woven structure extends over the entire surface of the insole.

Figure 4:
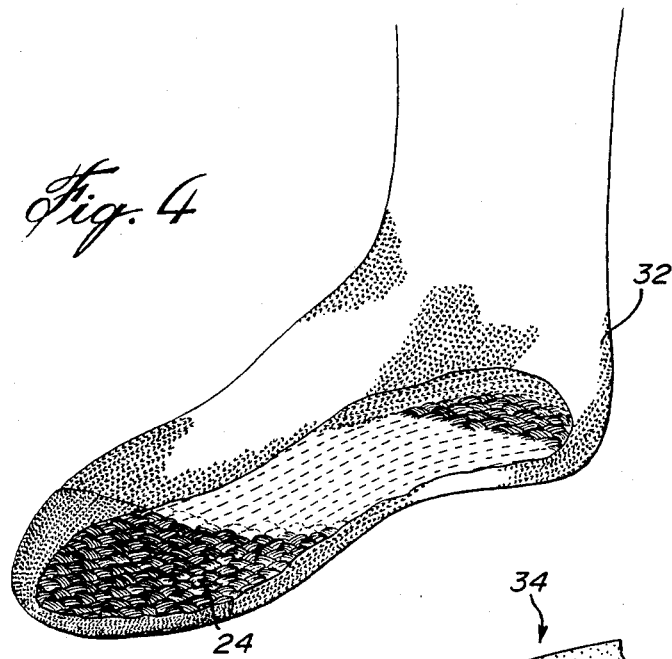
FIG. 4 is a perspective view of a sock device incorporating the biofeedback interface illustrated in FIG. 3.

Woven structure 24 may also be used for the construction of a shock-device 32, illustrated in FIG. 4 still for footwear applications. In such case, the woven structure 24 is applied on the portion of a sock, which faces the sole of the foot, such as by sewing or use of adhesives.

Woven structure 24 possesses certain advantages over the structure of the biofeedback interface 10, such as lower manufacturing cost and it is also relatively thin which is useful for certain applications.

The biofeedback interfaces described with relation to FIGS. 2, 3, and 4 are provided with fixed projections or irregularities which in use stimulate the skin always at the same places. As a result, after a period of time, the individual may get accustomed to the created discomfort (adaptation), which for all practical purposes results in a reduction of the sensation enhancement. This is especially true when the biofeedback interface is used in footwear applications in which case the biofeedback interface is confined in the shoe and remains stationary with respect of the foot.

Figure 5:
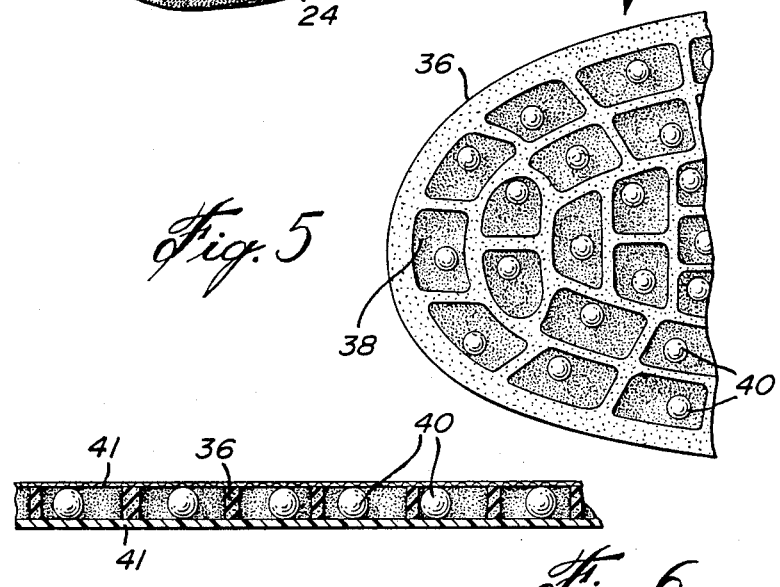
FIG. 5 is a plan view of a biofeedback interface for footwear applications with non-fixed irregularities, some elements being omitted.
Figure 6:
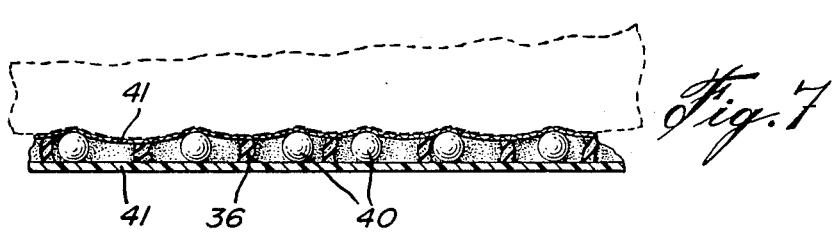
FIG. 6 is a vertical sectional view of the biofeedback interface shown in FIG. 5, in unloaded condition.
Figure 7:
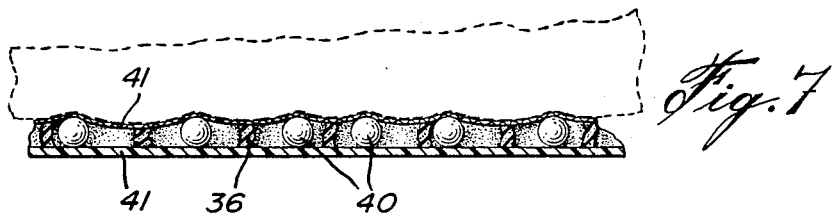
FIG. 7 is a vertical sectional view of the biofeedback interface shown in FIG. 5, in loaded condition.

To avoid this disadvantage, it is suggested to use a biofeedback interface with non-fixed or movable irregularities, such as the insole 34, illustrated in FIGS. 5, 6 and 7. Insole 34 comprises a relatively thick layer 36 of foamed-like plastic material comprising a plurality of openings 38. Openings 38 distributed over the entire surface of the insole 34, define cages or compartments receiving loose, relatively hard particles or fragments 40 such as spheres which are sufficiently small so as to be capable of moving in their respective compartments.

Foam-like layer 36 is mounted between two layers of synthetic material 41 which close the compartments defined by openings 38.

The resiliency of foam-like layer 36 is of importance and should comply with the following criteria;

(a) it should be sufficiently soft wherein when the biofeedback interface is loaded as shown in FIG. 7, the major portion of the weight is supported by the particles or fragments 40; and (b) it should have a sufficient memory wherein when it is unloaded, as illustrated in FIG. 6, in other words when the foot of the individual is momentarily in the air during walking or running it should spring back to its original shape allowing the particles 40 to move in their compartments.

When these two criteria are met, the particles 40 will slightly move in their respective compartments during walking or running to induce sensation to the foot at different places at each step.

Although the invention has been described with relation to specific forms, it will be evident for a person skilled in the art that it may be refined and modified in various ways. It is, therefore, wished to have it understood that the present invention should not be limited in interpretation except by the terms of the following claims.

I claim:

1. A biofeedback interface adapted to be interposed between an integument of a foot of an individual and a sole of a footwear, a relatively high level of loading being exerted between said foot and said sole, said biofeedback interface comprising sensation enhancement means for substantially enhancing the sensation perceived by said individual, potentially up to pain level, the sensation enhancement inducing a feedback reaction by said individual tending to adopt a posture for reducing the level of sensation perceived by said individual resulting in a moderation of the loading of said foot, said biofeedback interface including a plurality of compartments, each compartment receiving a loose relatively hard sensation enhancement member substantially smaller than said compartment for moving therein with respect said foot.

2. A biofeedback interface as defined in claim 1, wherein said biofeedback interface includes a layer of compressible and resilient material provided with a plurality of openings which define said compartments, said layer being also provided with a pair of additional thin layers mounted on top and bottom respectively on said layer of compressible and resilient material to close said openings.

3. A biofeedback interface as defined in claim 1, wherein said compartments are distributed under substantially the entire plantar surface of said foot.

4. A biofeedback interface as defined in claim 1, wherein said compartments are distributed over substantially an entire zone of the plantar surface of said foot encompassing the metatarsal-phalangeal joints of said foot.

5. An athletic shoe adapted to receive a foot of an individual and comprising insole means on which said foot rests, said insole means comprising sensation enhancement means for substantially enhancing the sensation perceived by said individual, potentially up to pain level, the sensation enhancement inducing a feedback reaction by said individual tending to adopt a posture for reducing the level of sensation perceived by said individual resulting in a moderation of the loading of said foot, said insole means including a plurality of compartments, each compartment receiving a loose relatively hard sensation enhancement member substantially smaller than said compartment for moving therein with respect to said foot.

6. An athletic shoe as defined in claim 5, wherein said insole means includes a layer of compressible and resilient material provided with a plurality of openings which define said compartments, said layer being also provided with a pair of additional thin layers mounted on top and bottom respectively on said layer of compressible and resilient material to close said openings.

7. An athletic shoe as defined in claim 5, wherein said compartments are distributed under substantially the entire plantar surface of said foot.

8. An athletic shoe, as defined in claim 5, wherein said compartments are distributed over substantially an entire zone of the plantar surface of said foot encompassing the metatarsal-phalangeal joints of said foot.

* * * * *